(12) United States Patent
Da Re et al.

(10) Patent No.: US 6,313,333 B1
(45) Date of Patent: Nov. 6, 2001

(54) MULTINUCLEAR CATIONIC PLATINUM COMPLEXES WITH ANTITUMOR ACTIVITY

(75) Inventors: Giovanni Da Re; Roberto Di Domenico, both of Milan; Silvano Spinelli, Monza, all of (IT); Nicholas Farrell, Richmond, VA (US)

(73) Assignee: Setanta Therapeutics, Inc., Richmond, VA (US)

( * ) Notice: Subject to any disclaimer, the term of this patent is extended or adjusted under 35 U.S.C. 154(b) by 0 days.

(21) Appl. No.: 09/446,867

(22) PCT Filed: Jul. 1, 1998

(86) PCT No.: PCT/EP98/04057

§ 371 Date: Apr. 27, 2000

§ 102(e) Date: Apr. 27, 2000

(87) PCT Pub. No.: WO99/01462

PCT Pub. Date: Jan. 14, 1999

(30) Foreign Application Priority Data

Jul. 4, 1997 (IT) ............................................ MI974001594

(51) Int. Cl.$^7$ .......................... C07F 15/00; A61K 31/282
(52) U.S. Cl. .......................... 556/137; 514/592; 544/225; 546/2; 548/101; 548/402; 549/3
(58) Field of Search ............................ 556/137; 514/592; 544/225; 546/2; 548/101, 402; 549/3

(56) References Cited

FOREIGN PATENT DOCUMENTS

| WO995/26968 | 10/1995 | (WO) . |
| WO96/16068 | 5/1996 | (WO) . |
| WO-01/13914-A1 | 3/2001 | (WO) . |

OTHER PUBLICATIONS

H. Rauter et al; Selective Platination of Biologically Relevant Polyamines, Linear Coordinating Spermidine and Spermine as Amplifying Linkers on Dinuclear Platinum Complexes; 6001 Chemical Abstracts, Columbus, Ohio; No CP–002056581; Inorg. Chem. 1997, 36 (18), 3919–3927 (eng.) American Chemical Society.

*Primary Examiner*—Porfirio Nazario-Gonzalez
(74) *Attorney, Agent, or Firm*—McGuireWoods, LLP

(57) ABSTRACT

The present invention relates to tetra- and penta-nuclear platinum complexes with antitumor activity, to a method for preparing them and to pharmaceutical compositions containing them.

20 Claims, No Drawings

MULTINUCLEAR CATIONIC PLATINUM COMPLEXES WITH ANTITUMOR ACTIVITY

The present invention relates to tetra- and penta-nuclear platinum complexes with antitumor activity, to a method for preparing them and to pharmaceutical compositions containing them.

STATE OF THE ART

The use of platinum complexes in the antitumor chemotherapy is well known. A number of platinum complexes, such as cis-platin, are used in the treatment of testicular, ovarian, head and neck and small cell lung carcinomas. However, the treatment with cis-platin may result in severe nephrotoxicity. A further clinical disadvantage is the problem of acquired drug resistance resulting in the tumor becoming refractory to treatment by the agent.

It is generally believed that platinum complexes such as cis-platin manifest their biological activity through covalent interaction with DNA. In partcular, cis-platin induces the formation of a range of adducts on DNA including monodentate adducts, bidentate adducts, such as GG or AG, and GNG intrastrand crosslinks [Reedijk et al., Structure and Bonding, 67, 53–89 (1987)]. To a lesser extent, cis-platin also results in interstrand GG crosslinks and DNA-protein crosslinks [Rahmouni et al., Biochemistry, 26, 7229–7234 (1987)]. These DNA lesions result in conformational changes which are reflected in bending and local unwinding of the DNA. These DNA lesions have been reported to inhibit the activity of various DNA polymerases [Vallan et al., Nucl. Acids Res., 16, 4407–4418 (1988); Pinto et al., Proc. Natl. Acad. Sci., 82, 4616–4619 (1985); Gralla et al., Cancer Res., 47, 5092–5096 (1987)]. The interstrand crosslink between two neighboring guanine bases has also been shown to inhibit RNA polymerase function [Lemaire et al., Proc. Natl. Acad. Sci., 88, 1982–1985 (1991)]. Accordingly, the cytotoxic effects of cis-platin are most likely attributable to the combined effects of these DNA lesions, rather than the result of any one specific lesion event.

Mono(platinum) and bis(platinum) complexes, containing respectively one or two platinum atoms, are compounds known in the art (U.S. Pat. Nos. 4,225,529, 4,250,189, 4,533,502, 4,565,884, 4,571,335 e 4,797,393).

Examples of tri-nuclear platinum complexes (also named tri-platinum complexes) were recently reported in the letterature [Yun Qu et al., Inorg. Chem., 32, 2591–2593 (1993)]. Said compounds, in which the ligands have a cis configuration, are complexes neutral or bearing an overall charge of +2 and they can be represented by the following general formulae:

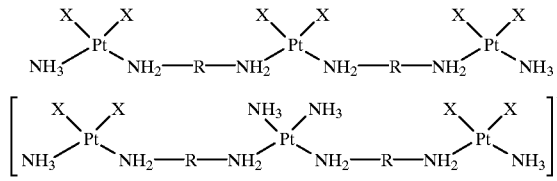

in which X means a labile ligand (such as a chlorine atom) and R means an alkylene chain. It can be seen that, in the case of the complexes with an overall charge of +2, said charge is located on the central platinum atom, bearing four neutral ligands, whereas the two peripheral platinum atoms are formally neutral and. as defined above, bifunctional.

WO95/26968 describes tri-platinum complexes in which the three platinum atoms are linked by diamine chains and in which the central platinum atom coordinates four neutral ligands, whereas the two peripheral platinum atoms coordinates each three neutral ligands and one ligand having −1 charge.

Such compounds have an overall charge of +4 and in particular the central platinum atom bears a formal charge of +2 and the two periferal platinum atoms bear a formal charge of +1 each. Moreover, the two periferal platinum atoms are monofunctional.

We have now found that by increasing the number of platinum cores linked by diamine ligands, new platinum complexes endowed with high antitumor activity are obtained.

In particular, the invention relates to tetra- and penta-platinum complexes of formula (I):

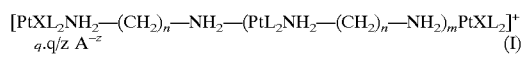

wherein
n is an integer from 2 to 7;
m is the integer 2 or 3;
X is selected in the group consisting of chlorine, bromine, iodine, $(C_1-C_4)$alkyl-carboxylate, di-$(C_1-C_4)$ alkylsulfoxide;
L is independently selected in the group consisting of ammonia, $(C_1-C_8)$alkyl-amine, di$(C_1-C_8)$alkyl-amine or is an heterocyclcle selected in the group consisting in pyridine, quinoline, isoquinoline, imidazole, thiazole, pyrimidine, purine, acridine, pyrazole, benzimidazole, benzothiazole.

$A^{-z}$ is a pharmaceutically accetable anion.

The complex's charge +q depends both on the number of the platinum cores present and on the nature of the X ligand. In particular, when the X ligand is a group bearing a negative charge, then the charge +q is given by the formula $$q=2m+2$$

in which m is as above defined.

However, when the X ligand is a neutral molecule, then the charge +q is determined by the following formula $$q=2m+4$$

The expert of the art will appreciate the fact that the ligands may be in cis or trans position with respect to the platinum atom:

In the present invention are included all the possible isomers, enantiomers and diastereoisomers of the compounds of formula (I). More particularly, compounds of formula (I) in which m is the integer 2 and 3 respectively, are represented by the general formulae (Ia) and (Ib):

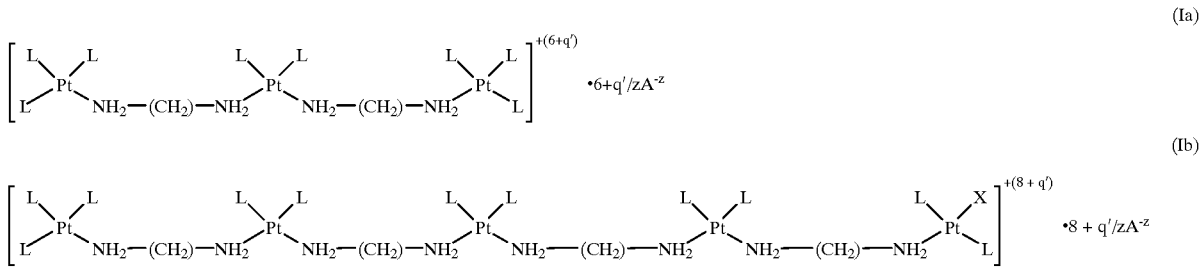

wherein X, L and $A^{-z}$ have the meanings above defined, n is an integer which independently ranges from 2 to 7 and q' is 0 if X is a ligand with −1 charge or the integer 2 if X is a neutral ligand.

The stereochemistry of the ligands in the formulae (Ia) and (Ib) is just indicative, being encompassed in the invention, as said above, all the possible stereoisomers.

The X ligands are preferably selected in the group consisting of chlorine, bromine and iodine.

The ligands L are preferably ammonia.

$A^{-z}$ is preferably selected in the group consisting of chloride, bromide, iodide, nitrate. sulfate, hydrogensulfate, perchlorate.

Tetra- and penta-platinum complexes having the same n value inside the molecule, that is in which the various platinum cores are linked by the same diamine, are preferred.

Preferred compounds of formula (I) are those in which the ligands are in position trans with respect to the platinum atom.

Particularly preferred compounds of formula (I) are those in which X is selected in the group consisting of chlorine, bromine and iodine, L is ammonia and $A^{-z}$ is selected in the group consisting of chloride, bromide, iodide, nitrate, sulfate, hydrogensulfate, perchlorate and in which the stereochemistry of platinum core's ligands is trans.

Even more particularly preferred compounds of formula (I) are those in which, in addition to the above limitations, n is the integer 6.

The present invention encompasses also methods for obtaining the compounds of formula (I).

The compounds of formula (Ia) are prepared according to scheme 1.

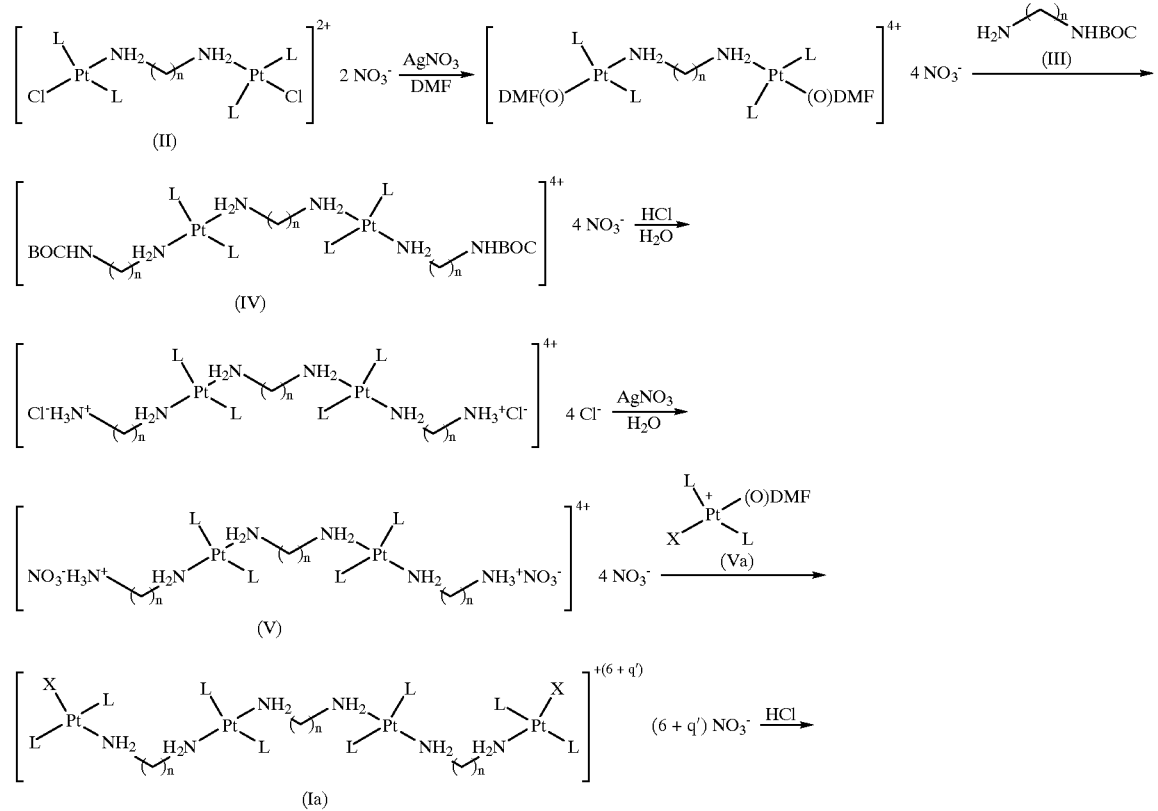

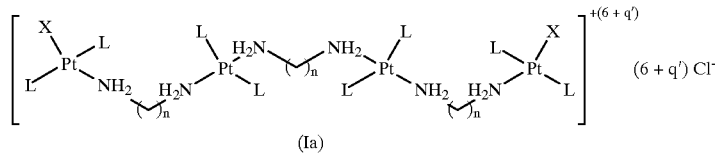

(Ia)

In particular, such a synthesis scheme comprises the following steps:

(a) activation of the bis-platinum complex of formula (II) through substitution of the two chlorine atoms with two molecules of dimethylformamide and subsequent reaction of the so obtained intermediate with two equivalents of mono-protected diamine of formula (III), to give the intermediate of formula (IV);

(b) removal of the two protecting groups of the amines from intermediate of formula (IV) and subsequent optional exchange of the counterion so obtained with nitrate ion to give the intermediate of formula (V);

(c) reaction of the intermediate of formula (V) with two equivalents of platinum complex of formula (Va) to give compounds of formula (Ia);

(d) optional transformation of one compound of formula (Ia) into another compound of formula (Ia) having a different counterion, by means of exchange reaction of said counterion with the wanted anion.

The compounds of formula (II) are known and can be prepared according to the method described in WO 91/03482, which encompasses the reaction of two equivalents of trans- or cis-platinum with a α,ω-alkanediamine in water overnight.

The compounds of formula (Va) can be prepared from the known platinum complexes of formula [PtClXL2] according to the method described in WO 95/26968.

The compounds of formula (Ib) can be prepared according to scheme 2.

Scheme 2

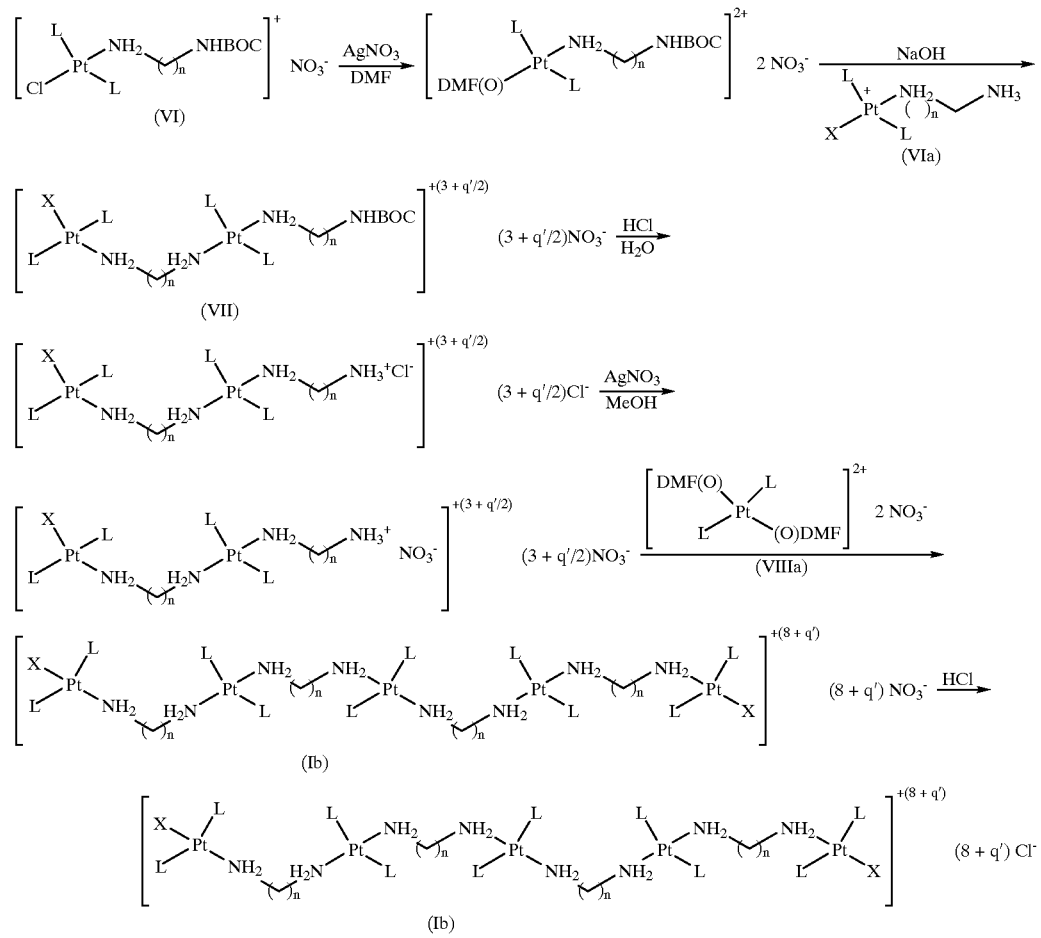

In particular, Such a synthesis scheme comprises the following steps:

(e) activation of the intermediate of formula (VI) through exchange of one chlorine atom with a molecule of dimethylformamide and subsequent reaction of the intermediate so obtained with one equivalent of intermediate of formula (VIa), to give the complex of formula (VII);

(f) removal of the aminic protecting group from the complex of formula (VII) and subsequent exchange reaction of the counterion so obtained with nitrate ion, obtaining the intermediate of formula (VIII);

(g) reaction of two equivalents of intermediate (VIII) with one equivalent of platinum complex of formula (VIIIa) to give a compound of formula (Ib);

(h) optional transformation of one compound of formula (Ib) into another compound of formula (Ib) having a different counterion by means of exchange reaction of said counterion with the wanted anion.

The compounds of formula (VI) can be prepared from the known platinum complexes of formula [PtCl2L2] according to the method described in WO 95/26968. The compounds of formula (VIa) can be prepared from the corresponding compounds of formula (VI) by removal of the aminic protecting group. The reaction scheme is the same if X is different from chlorine. In this latter case the starting complex will be [PtClXL2].

The compounds of formula (VIIIa) can be prepared starting from the known platinum complexes of formula [PtCl2L2] as described in WO 95/26968.

The stereochemistry shown in schemes 1 and 2 is just indicative, being possible to obtained the wanted stereochemistry starting from the suitable mono-platinum complex intermediate.

The expert in the field will appreciate the fact that in intermediates of formula (III) and (VI), alternatively to the BOC (tert-butoxycarbonyl) group, can be used other known protecting groups of primary amines, such as those reported in Green, T. W., Wuts, P. G. M., "Protective Groups in Organic Synthesis", second edition, John Wiley & Sons, 1991.

In the case the protecting group which is used is the tert-butoxycarbonyl group, reaction conditions for its removal are those which encompass the use of inorganic acids (for example, hydrochloric acid) or organic acids (for example, trifluoroacetic acid), optionally in water medium. Preferred conditions are those which encompass the use of hydrogen chloride in alcoholic solution.

Activation reaction of the platinum complexes with dimethylformamide and subsequent reaction for the formation of Pt-N bonds are performed according to the methods described in WO 95/26968. In particular, preferred conditions for the activation reaction are those which encompass the use of dimethylformamide as the solvent and slight excess of silver nitrate with respect to the platinum complex equivalents, at temperatures ranging from room temperature to 40° C. Preferred conditions for the reaction of formation of the Pt-N bond are those which encompass the use of a dipolar aprotic solvent such as dimethylformamide and at temperatures ranging from −20° C. to 50° C.

An alternative process for the preparation of the complexes of formula (Ib) encompasses the reaction of the intermediate of formula (IX):

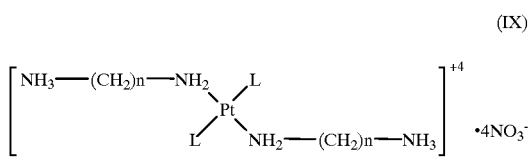

with two equivalents of ontermediate of formula (VI), to give, after removal of the aminic protecting group present, the tri-platinum complex of formula (X):

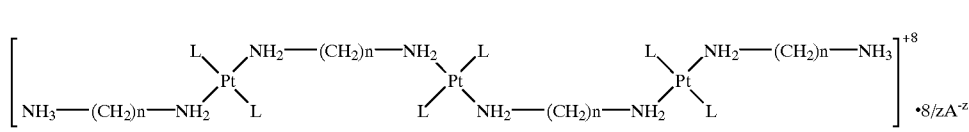

The intermediate (X) is then submitted, if necessary, to an exchange reaction of the anion $A^{-z}$ with nitrate anion and finally it is reacted with two equivalents of intermediate of formula (Va), to give the compounds of formula (Ib). The intermediate of formula (IX), if L is ammonia, is known or in any case can be prepared as described in WO 95/26968.

The compounds of the invention are endowed not only with a high antitumor activity, but also with a low toxicity and therefore their therapeutic index is particularly favourable.

The compounds of the invention were evaluated "in vitro" for their cytotoxix effect on various tumor cell lines, among which L-1210, A2780 or L-1210 and A2780 resistent to cis-platin. Table I shows a comparison data between one compound of the invention and some prior art compounds.

TABLE I

"in vitro" cytotoxic activity against murine leukemia L1210

| Compound | type | $IC_{50}$ µg/ml |
|---|---|---|
| t,t,t,t,t-[PtCl(NH$_3$)$_2$H$_2$N—(CH$_2$)$_6$—NH$_2$Pt(NH$_3$)$_2$H$_2$N—(CH$_2$)$_6$— NH$_2$Pt(NH$_3$)$_2$H$_2$N—(CH$_2$)$_6$—NH$_2$Pt(NH$_3$)$_2$H$_2$N—(CH$_2$)$_6$— | penta-Pt | 0.3 |

TABLE I-continued

"in vitro" cytotoxic activity against murine leukemia L1210

| Compound | type | IC$_{50}$ μg/ml |
|---|---|---|
| NH$_2$PtCl(NH$_3$)$_2$]$^{+8}$.8Cl$^-$ t,t,t-[PtCl(NH$_3$)$_2$H$_2$N(CH$_2$)$_6$NH$_2$Pt(NH$_3$)$_2$H$_2$N(CH$_2$)$_6$NH$_2$ PtCl(NH$_3$)$_2$]$^{+4}$.4NO$_3^-$ | tri-Pt | 0.38 |
| t,t-[PtCl(NH$_3$)$_2$H$_2$N—(CH$_2$)$_6$—NH$_2$PtCl(NH$_3$)$_2$]$^{+2}$.2NO$_3^-$ | bis-Pt | 2.3 |
| cis-platin (CDDP) | mono-Pt | 0.9 |

From the data reported in Table I it can be seen a steady increase in the activity from mono-/bis-platinum complexes to tri- and penta-platinum complexes. Moreover, the compounds of the invention were evaluated in an "in vivo" test in which L-1210 tumor is inoculated intra peritoneum in the rat and the compound is administered intra peritoneum after 24, 120 and 216 hours from the tumor inoculation. The compounds of the invention showed a high cytotoxic affect on both the experimental models.

The platinum complexes of the present invention resulted particularly active when administered in association with other platinum complexes, showing synergic effect with them.

The compounds of formula (I), when administered to men and animals bearing tumors susceptible of treatment with platinum complexes, in doses ranging from 1 mg to 1.2 g per square metre of body area, are able to induce the regression of the said tumor forms.

The effective dosage of the compounds of the invention can be determined by an expert clinician with known and conventional methods. The correlation between the dosages used with animals of various species and size and with the human (on the base of mg/m2 of body area) is described in Freirech, E. J. et al., Quantitative Comparison of Toxicity of Anticancer Agents in Mouse, Rat, Hamster, Dog, Monkey and Man, Cancer Chemother. Rep., 50, N. 4, 219–244 (1966).

Usually however dosages of the complex from 1 to 1200 mg/kg will be administered to the patient, with a dosage regimen which will vary depending on several factors well known to the clinician expert in the art.

Sometimes it will be advantageous to administer the platinum complex of the present invention with one or more agents which enhance the antitumor activity or which decrease the undesirable side effects of the platinum complex. For example, the platinum complexes of the present invention may be administered along with reduced glutathione, as described in GB 2174905 and U.S. Pat. No. 4,871,528.

The tumors in the patients which can be treated with the platinum complexes of the present invention are those tumors which are known to be susceptible to cis-platin therapy. The complexes of the present invention are also active against certain tumor resistant to cis-platin.

More generally, the compounds of the invention can be used for the treatment of the same pathologies for which cis-platin is used. This includes the treatment of tumors, sensitization or enhancement of radiation [Douple et al., Cisplatin Current Status and Developments, Ed. A. W. Prestayk et al., Academic Press, 125 (1980); Douple et al., Platinum Metals Res., 29, 118 (1985)] and the treatment of parasytic illnesses such as sleeping sickness [Farrell et al., Biochem. Pharmacol. 33, 961 (1984)].

The regimen of treatment can be suitably varied as it is well known to the clinician expert in the treatmet of the tumor forms, depending on the kind of the tumor to be treated and on the conditions of the patient.

The compounds of the invention are preferably administered as sterile aqueous solutions. The solution are preferably administered via endovenous or intra-arterial route, although other administration forms may be suitable in particular cases.

The pharmaceutical forms which can be used for parenteral administration encompass sterile aqueous solutions or sterile powders for the extemporaneous preparation of the solutions, as well as oily preparations for intramuscular or intraperitoneal administration.

Other suitable pharmaceutical forms can be syrups or similar liquid forms, as well as solid forms such as tablets, capsules or the like.

Other possible examples of suitable pharmaceutical forms for example are those reported in Remington's Pharmaceutical Sciences.

The following examples further illustrate the invention.

PREPARATION 1

N-BOC hexanediamine is prepared starting from its hydrochloride salt, which is a commercial product.

2.1 g of N-BOC hexanediamine hydrochloride are dissolved in ethyl ether (20 ml) and treated under stirring with 16 ml of a 1 N sodium hydroxide aqueous solution.

The organic phase is then washed with brine, dried over sodium sulfate and the solvent is evaporated under reduced pressure, obtaining N-BOC hexanediamine free base in theoretical yield.

PREPARATION 2

Synthesis of trans-[PtCl(NH$_3$)$_2$H$_2$N—(CH$_2$)$_6$—NH—BOC]$^+$NO$_3^-$—intermediate (VI)

2 g of trans-platin are dissolved in 133 ml of anhydrous dimethylformamide and are added with 1.13 g of silver nitrate. The reaction mixture is kept under stirring shielded from the light for 18 hours. After such a time, the precipitated silver chloride is removed by filtration and the clear filtrate is cooled to −20° C. and added with a solution of N-BOB-1,6-hexanediamine (1.36 g) in 40 ml of anhydrous DMF. The addition lasts for about 30 minutes. The solution is kept under stirring at −20° C. for 3 hours and at room temperature for 1 hour. The solvent is then evaporated under reduced pressure and the residue is treated with 200 ml of ethyl ether, kept under stirring for 20 minutes, then it is filtered. The resulting solid is dissolved in 200 ml of methanol and kept under stirring for 1 hour in order to eliminate any traces of trans-platin by precipitating it. The separated trans-platin is eliminated by filtration and the solution is treated with active carbon, it is filtered again and finally the solvent is evaporated under reduced pressure. The residue is treated with acetone (100 ml) and filtered to give 2.3 g of the product.

Elemental analysis (calcd/found %): C 24.33/24.05; H 5.57/5.64; N 12.90/12.84; Cl 6.53/6.40; Pt 35.93/36.06.

$^{195}$Pt-NMR in DMF/d7-DMF: −2433 ppm

PREPARATION 3

Synthesis of trans-[PtCl(NH$_3$)$_2$H$_2$N—(CH$_2$)$_6$—NH$_3$]$^{2+}$ 2NO$_3^-$—intermediate (VIa)

To a solution of 1.5 g of [PtCl(NH$_3$)$_2$H$_2$N—(CH$_2$)$_6$—NH—BOC]$^+$NO$_3^-$— in 150 ml of methanol are added 21 ml of 6.5 M hydrogen chloride solution in ethanol. The reaction mixture is kept under stirring for 24 hours at room temperature, then the solid is filtered, washed on the filter with methanol and ethyl ether and finally it is dried.

The solid so obtained is dissolved in 180 ml of methanol and added with a solution of silver nitrate (0.825 g) in 45 ml of methanol. The reaction mixture is kept under stirring at room temperature for 30 minutes, the silver chloride is eliminated by filtration and the clear filtrate is evaporated to dryness. The residue is treated with acetone, kept under stirring for 15 minutes, filtered and dried, to give 0.925 g of the product.

Elemental analysis (calcd/found %): C 14.16/14.19; H 4.58/4.66; N 16.61/16.62; Cl 7.01/6.91; Pt 38.57/36.10. $^{195}$Pt-NMR in DMF/d7-DMF: −2433 ppm

PREPARATION 4

Synthesis of trans-[BOCNH—(CH$_2$)$_6$—NH$_2$—Pt(NH$_3$)$_2$H$_2$N—(CH$_2$)$_6$—NHBOC]$^{2+}$2NO$_3^-$—intermediate (IX)

To a suspension of 1.028 g of trans-platin in 35 ml of anhydrous dimethylformamide are added 1.16 g of silver nitrate. The reaction mixture is heated at 60° C., shielded from the light, for 5 hours, then the precipitated silver chloride is removed by filtration. A solution of N-BOC-1, 6-hexanediamine (1.48 g) in 5 ml of dimethylformamide is then added and the resulting reaction mixture is kept at room temperature overnight. By diluting with 300 ml of ethyl ether a white solid separates which is filtered, redissolved in methanol and filtered through a 0.2 micron Millex filter to remove the traces of silver salts. The methanolic solution is then diluted with ethyl ether. A white solid crystallizes, which is filtered and dried, obtaining 1.94 g of the product.

Elemental analysis (calcd/found %): C 33.63/33.44; H 6.93/7.00; N 14.26/14.30; Pt 24.83/25.06. $^{195}$Pt-NMR in DMF/d7-DMF: −2687 ppm.

PREPARATION 5

Synthesis of trans-[NH$_3$—(CH$_2$)$_6$—NH$_2$—Pt(NH$_3$)$_2$H$_2$N—(CH$_2$)$_6$—NH$_3$]$^{4+}$4Cl$^-$ 500 mg of trans-[BOC—NH—(CH$_2$)$_6$—NH$_2$—Pt(NH$_3$)$_2$H$_2$N—(CH$_2$)$_6$—NH—BOC]$^{2+}$2NO$_3^-$ are dissolved in 50 ml of methanol and added with 5 ml of 6.5 M hydrogen chloride solution in ethanol. The reaction mixture is kept under stirring at room temperature for 42 hours, then the solid is filtered and washed with ethyl ether, obtaining 340 mg of the product.

Elemental analysis (calcd/found %): C 23.81/23.14; H 6.66/6.73; N 13.88/13.51; Cl 23.42/22.03; Pt 32.23/31.68. $^{195}$Pt-NMR in water: −2674 ppm.

PREPARATION 6

Synthesis of cis-[BOC—NH—(CH$_2$)$_6$—NH$_2$—Pt(NH$_3$)$_2$H$_2$N—(CH$_2$)$_6$—NH—BOC]$^{2+}$2NO$_3^-$—intermediate (IX)

To a solution of cis-platin (3 g) in 100 ml of dimethylformamide, kept at room temperature, under stirring and in inert gas atmosphere, 3.4 g of silver nitrate are added. After 19 hours at room temperature, the precipitated silver chloride is eliminated by filtration by passing the suspension through a cellulose filter placed over a microfibre filter, then through a double microfibre filter. The yellow solution so obtained is kept under stirring and added with a solution of 4.54 g of N-BOC hexanediamine in 12 ml of dimethylformamide. After keeping it under stirring overnight, the resulting reddish mixture is decoloured with active carbon (1.5 g), filtered and the solvent is eliminated by evaporation under reduced pressure. The residue (dark yellow oil) is redissolved in 60 ml of methanol and filtered through 0.2 micron Millex filter. The clear solution is evaporated to dryness and the yellow oily residue is treated with 350 ml of ethyl ether. By filtering the sprecipitated solid in drying it in an oven, 6.94 g of the product are obtained. Elemental analysis (calcd/found %): C 33.63/33.48; H 6.93/6.99; N 14.26/14.17; Pt 24.83/25.13. $^{195}$Pt-NMR in d7-DMF: −2681 ppm.

PREPARATION 7

Synthesis of cis-[NH$_3$—(CH$_2$)$_6$—NH$_2$—Pt(NH$_3$)$_2$H$_2$N—(CH$_2$)$_6$—NH$_3$]$^{4+}$4Cl$^-$ To a solution of cis-[EBOC—NH—(CH$_2$)$_6$—NH$_2$—Pt(NH$_3$)$_2$H$_2$N—(CH$_2$)$_6$—NH—BOC]$^{2+}$2NO$_3^-$ (100 mg) in 1.5 ml of methanol, kept under stirring and at room temperature, 1.39 ml of a 4.11 N hydrogen chloride solution in ethanol are added. After about 1 hour a solid begins to separate, which from white changes to yellowish colour. After 23 hours the solid is filtered, washed on the filter with the mother liquors and then with ethyl ether and finally it is dried in an oven at 40° C. overnight. 62 mg of the product are obtained.

Elemental analysis (calcd/found %): C 23.81/23.10; H 6.66/6.21; N 13.88/13.57; Cl 23.42/22.69; Pt 32.23/32.92.

PREPARATION 8

Synthesis of trans-[PtCl(NH$_3$)$_2$(DMF)]+.NO$_3^-$—intermediate (Va)

To a solution of trans-platin (2 g) in 210 ml of anhydrous dimethylformamide 1.13 g of silver nitrate are added and the reaction mixture is kept in the darkness at room temperature for 24 hours. The formed silver chloride is eliminated by filtration and the clear solution is used as such in the subsequent reaction.

PREPARATION 9

Synthesis of trans-[Pt(NH$_3$)$_2$(DMF)$_2$]$^{+2}$.2NO$_3^-$—intermediate (VIIIa)

61 mg of trans-platin are suspended in 5.8 ml of anhydrous dimethylformamide and are added with 69.1 mg of silver nitrate. The reaction mixture is kept under stirring in the darkness and at 65° C. for 6 hours, then it is cooled to room temperature and the precipitated silver chloride is removed by filtration. The clear solution is used as such in the subsequent reaction.

PREPARATION 10

Synthesis of trans-[NH$_3$—(CH$_2$)$_6$—NH$_2$—Pt(NH$_3$)$_2$H$_2$N—(CH$_2$)$_6$—NH$_3$]$^{4+}$4NO$_3^-$—

To a solution of 12 g of trans-[NH$_3$—(CH$_2$)$_6$—NH$_2$—Pt(NH$_3$)$_2$H$_2$N—(CH$_2$)$_6$—NH$_3$]$^{4+}$4Cl$^-$ (preparation 5) in 395 ml of distilled water 13.46 g of silver nitrate are added and the reaction mixture is kept in the darkness under stirring for 30 minutes, then it is filtered. The filtrate is concentrated to 45 ml and added with 1.2 l of acetone. After 1 hour under stirring the formed solid is filtered and washed on the filter with 50 ml of acetone, obtaining 13.68 g of the product.

EXAMPLE 1

Synthesis of t,t-[BOCNH—(CH$_2$)$_6$—NH$_2$—Pt(NH$_3$)$_2$—H$_2$N—(CH$_2$)$_6$—NH$_2$—Pt(NH$_3$)$_2$—H$_2$N—(CH$_2$)$_6$—NHBOC]$^{+4}$.4NO$_3^-$—intermediate (IV)

462 mg of t,t-[PtCl(NH$_3$)$_2$—H$_2$N—(CH$_2$)$_6$—NH$_2$—PtCl(NH$_3$)$_2$]$^{+2}$.2NO$_3^-$ (prepared according to the method described in WO 91/03482) are dissolved in 13 ml of anhydrous dimethylformamide, by heating at 50° C., then 204 mg of silver nitrate are added to the solution and it is kept under stirring at 50° C. and shielded from the light for about 1 hour. The reaction mixture is cooled and filtered,

EXAMPLE 2

Synthesis of t,t-[NH$_3$—(CH$_2$)$_6$—NH$_2$—Pt(NH$_3$)$_2$—H$_2$N—(CH$_2$)$_6$—NH$_2$—Pt(NH$_3$)$_2$—H$_2$N—(CH$_2$)$_6$—NH$_3$]$^{+6}$.6NO$_3^-$—intermediate (V)

To a suspension of t,t-[BOCNH—(CH$_2$)$_6$—NH$_2$—Pt(NH$_3$)$_2$—H$_2$N—(CH$_2$)$_6$—NH$_2$—Pt(NH$_3$)$_2$—H$_2$N—(CH$_2$)$_6$—NHBOC]$^{+4}$.4NO$_3^-$ (680 mg; example 1) in 35 ml of methanol 12 ml of concentrated hydrochloric acid are added and the reaction mixture is kept under stirring over night. The mixture is then diluted with tert-butyl methyl ether and kept under stirring overnight. 440 mg of the product as hydrochloride salt are obtained by filtration.

The solid so obtained is dissolved in 25 ml of water and added with 440 mg of silver nitrate. After 40 minutes under stirring in the darkness, the reaction mixture is filtered and the solvent is evaporated under reduced pressure. The residue is treated with tert-butyl methyl ether, kept under stirring for 30 minutes, filtered and dried under vacuum at 40° C. to give 470 mg of the product.

EXAMPLE 3

Synthesis of t,t,t,t-[PtCl(NH$_3$)$_2$H$_2$N—(CH$_2$)$_6$—NH$_2$Pt—(NH$_3$)$_2$H$_2$N—(CH$_2$)$_6$—NH$_2$Pt(NH$_3$)$_2$H$_2$N—(CH$_2$)$_6$—NH$_2$PtCl—(NH$_3$)$_2$]$^{+6}$.6Cl$^-$.3H$_2$O – compound (Ia)

Ta solution of the intermediate of the example 2 (470 mg) in 5 ml of anhydrous dimethylformamide 0.865 ml of 0.92 N sodium hydroxide solution in methanol are added under stirring. After 5 minutes the resulting mixture is added with 32.5 ml of the solution containing mono-activated trans-platin (preparation 8). After one night under stirring, the reaction mixture is poured into 60 ml of tert-butyl methyl ether. After 1 hour under stirring, the formed solid is filtered, redissolved in 0.1 N hydrochloric acid (25 ml) at 45° C., then it is cooled to 30° C. and added with 50 mg of active carbon. After 45 minutes under stirring the solution is filtered to eliminate the carbon, then it is added with 310 mg of concentrated hydrochloric acid, by cooling to 5° C. with water/ice. After 1 night under stirring at room temperature, the white crystal is filtered, washed on the filter with 0.1 N hydrochloric acid and then with acetone and dried under vacuum at 40° C. The product so obtained is purified by silica gel chromatography, then it is dissolved in a 0.008 N sodium chloride solution (8 ml), filtered while warm, cooled and added with 1 ml of 4 N hydrochloric acid. After 1 hour the solid is filtered and dried under vacuum at 40° C. to give 65 mg of the pure product. $^{195}$Pt-NMR in d7-DMF: –2400 ppm; –2660 ppm.

Elemental analysis (% found/calcd): C 13.46/13.49; H 4.94/4.91; N 12.13/12.23; Cl 17.32/17.69; Pt 47.63/48.68.

EXAMPLE 4

According to the procedures described in the examples 1–3, starting from the suitable bis-platinum complexes and from the suitable α,ω-diamines, the following tetra-platinum complexes are prepared:

[Pt(MeCOO)(NH$_3$)$_2$H$_2$N—(CH$_2$)$_6$—NH$_2$Pt(NH$_3$)$_2$H$_2$N—(CH$_2$)$_6$—NH$_2$Pt—(NH$_3$)$_2$H$_2$N—(CH$_2$)$_6$—NH$_2$Pt(MeCOO)(NH$_3$)$_2$]$^{+6}$.6Cl$^-$;

[PtCl(MeNH$_2$)$_2$H$_2$N—(CH$_2$)6—NH$_2$Pt(MeNH$_2$)$_2$H$_2$N—(CH$_2$)$_6$—NH$_2$Pt—(MeNH$_2$)$_2$H$_2$N—(CH$_2$)$_6$—NH$_2$PtCl(MeNH$_2$)$_2$]$^{+6}$.6Cl$^-$;

[Pt(Me$_2$SO)(NH$_3$)$_2$H$_2$N—(CH$_2$)$_6$—NH$_2$Pt(NH$_3$)$_2$H$_2$N—(CH$_2$)$_6$—NH$_2$Pt—(NH$_3$)$_2$H$_2$N—(CH$_2$)$_6$—NH$_2$Pt(Me$_2$SO)(NH$_3$)$_2$]$^{+8}$.8Cl$^-$;

[PtCl(Et$_2$NH)$_2$H$_2$N—(CH$_2$)$_6$—NH$_2$Pt(Et$_2$NH)$_2$H$_2$N—(CH$_2$)$_6$—NH$_2$Pt— (Et$_2$NH)$_2$H$_2$N—(CH$_2$)$_6$—NH$_2$PtCl(Et$_2$NH)$_2$]$^{+6}$.6NO$_3^-$;

[PtCl(NH$_3$)$_2$H$_2$N—(CH$_2$)$_2$—NH$_2$Pt(NH$_3$)$_2$H$_2$N—(CH$_2$)$_2$—NH$_2$Pt—(NH$_3$)$_2$H$_2$N—(CH$_2$)$_2$—NH$_2$PtCl(NH$_3$)$_2$]$^+$6.6Cl$^-$;

[PtBr(NH$_3$)$_2$H$_2$N—(CH$_2$)$_7$—NH$_2$Pt(NH$_3$)$_2$H$_2$N—(CH$_2$)$_7$—NH$_2$Pt—(NH$_3$)$_2$H$_2$N—(CH$_2$)$_7$—NH$_2$PtBr(NH$_3$)$_2$]$^+$6.6NO$_3^-$;

[PtCl(MeNH$_2$)$_2$H$_2$N—(CH$_2$)$_4$—NH$_2$Pt(MeNH$_2$)$_2$H$_2$N—(CH$_2$)4—NH$_2$Pt—(MeNH$_2$)$_2$H$_2$N—(CH$_2$)$_4$—NH$_2$PtCl(MeNH$_2$)$_2$]$^{+6}$.6HSO$_4^-$;

[Pt(PrCOO)(NH$_3$)$_2$H$_2$N—(CH$_2$)$_3$—NH$_2$Pt(NH$_3$)$_2$H$_2$N—(CH$_2$)$_3$—NH$_2$Pt—(NH$_3$)$_2$H$_2$N—(CH$_2$)$_3$—NH$_2$Pt(PrCOO)(NH$_3$)$_2$]$^{+6}$.6Cl$^-$;

[PtCl(pyridine)$_2$H$_2$N—(CH$_2$)$_6$—NH$_2$Pt(NH$_3$)$_2$H$_2$N—(CH$_2$)$_6$—NH$_2$Pt—(NH$_3$)$_2$H$_2$N—(CH$_2$)$_6$—NH$_2$PtCl(pyridine)$_2$]$^{+6}$.6Cl$^-$;

[PtCl(imidazole)$_2$H$_2$N—(CH$_2$)$_6$—NH$_2$Pt(NH$_3$)$_2$H$_2$N—(CH$_2$)$_6$—NH$_2$Pt—(imidazole)$_2$H$_2$N—(CH$_2$)$_6$—NH$_2$PtCl(imidazole)$_2$]$^{+6}$.6Cl$^-$;

[PtCl(isoquinoline)$_2$H$_2$N—(CH$_2$)$_3$NH$_2$Pt(NH$_3$)$_2$H$_2$N—($_2$)$_3$—NH$_2$Pt(NH$_3$)$_2$H$_2$N—(CH$_2$)$_3$—NH$_2$PtCl(isoquinoline)$_2$]$^{+6}$.6Cl$^-$;

[PtCl(pyrazole)$_2$H$_2$N—(CH$_2$)$_7$—NH$_2$Pt(NH$_3$)$_2$H$_2$N—(CH$_2$)$_7$—NH$_2$Pt—(NH$_3$)$_2$H$_2$N—(CH$_2$)$_7$—NH$_2$PtCl(pyrazole)$_2$]$^{+6}$.6NO3$^-$.

EXAMPLE 5

Synthesis of t,t-[PtCl(NH$_3$)$_2$H$_2$N—(CH$_2$)$_6$—NH$_2$Pt(NH$_3$)$_2$H$_2$N—(CH$_2$)$_6$—NHBOC]$^{+3}$.3NO$_3^-$—intermediate (VII)

To a solution of 891 of of trans-[PtCl(NN$_3$)$_2$H$_2$N—(CH$_2$)$_6$—NHBOC]$^+$.NO$_3^-$ (intermediate (VI)—preparation 2) in 20 ml of anhydrous dimethylformamide, heated at about 40° C., 278 mg of silver nitrate are added. After 4 hours under stirring in the darkness and under nitrogen atmosphere, the reaction mixture is filtered.

To a solution of 830 mg of trans-[PtCl(NH$_3$)$_2$H$_2$N—(CH$_2$)$_6$—NH$_3$]$^{+2}$.2NO$_3^-$ (intermediate (VIa)—preparation 3) in 4.5 ml of anhydrous dimethylformamide, 1.6 ml of 1.02 M sodium hydroxide solution in methanol are added. After about 5 minutes the reaction mixture is added to the clear solution of the activated intermediate (VI). After 18 hours under stirring the dark mixture is diluted with the same volume of tert-butyl methyl ether. After additional 30 minutes under stirring 1.57 g of the product as a brown crystal are separated by filtration.

EXAMPLE 6

Synthesis of t,t-[PtCl(NH$_3$)$_2$H$_2$N—(CH$_2$)$_6$—NH$_2$Pt(NH$_3$)$_2$H$_2$N—(CH$_2$)$_6$—NH$_3$]$^{+4}$.4NO$_3$—intermediate (VIII)

A suspension of intermediate (VII) (1.5 g—example 5) in 45 ml of distilled water is added with 30 ml of concentrated hydrochloric acid. After stirring at room temperature overnight the reaction mixture is filtered and the obtained gummy solid is suspended in methanol and kept under stirring for about 30 minutes, obtaining 650 mg of t,t-[PtCl(NH$_3$)$_2$H$_2$N—(CH$_2$)$_6$—NH$_2$Pt(NH$_3$)$_2$H$_2$N—(CH$_2$)$_6$—NH$_3$]$^{+4}$.4Cl$^-$ as a brown solid.

The solid so obtained is suspended in 6.5 ml of distilled water, added with 509 mg of silver nitrate and kept under stirring in the darkness for 30 minutes. The reaction mixture is then filtered, the filtrate is evaporated under reduced pressure and the residue is diluted with acetone and kept under stirring overnight. By filtration 470 mg of yellow crystal are separated, which is redissolved in 12 ml of methanol and added with 4 ml of 8 N hydrogen chloride solution in ethanol. After stirring overnight, the obtained solid is filtered, dried and suspended again in distilled water. To such a suspension 349 mg of silver nitrate are added and after 30 minutes under stirring the reaction mixture is filtered and the solvent is evaporated off under reduced pressure. The residue is suspended in tert-butyl methyl ether and kept under stirring overnight, then the solid is filtered and dried under vacuum to give 420 mg of pure product.

EXAMPLE 7

Synthesis of t,t,t,t,t-[PtCl(NH$_3$)$_2$H$_2$N—(CH$_2$)$_6$—NH$_2$Pt—(NH$_3$)$_2$H$_2$N—(CH$_2$)$_6$—NH$_2$Pt(NH$_3$)$_2$H$_2$N—(CH$_2$)$_6$—NH$_2$Pt(NH$_3$)$_2$H$_2$N—(CH2)$_6$—NH$_2$PtCl(NH$_3$)$_2$]$^{+8}$.8Cl$^-$—compound (Ib)

A solution of intermediate (VIII) (420 mg—example 6) in 3 ml of anhydrous dimethylformamide is added with 0.469 ml of 0.92 N sodium hydroxide solution in methanol, then such a mixture is added with 4.8 ml of solution of bis-activated trans-platin (intermediate (VIIIa)—preparation 9). After 2 nights under stirring in the darkness, the reaction mixture is diluted with the same volume of tert-butyl methyl ether and after 1 hour under stirring the formed brown crystal is filtered. The solid is dissolved at 40° C. in 20 ml of 0.1 N hydrochloric acid and the solution is filtered while warm, then it is decoloured with active carbon (50 mg). The clear filtrate so obtained is added with about 240 ml of concentrated hydrochloric acid and after 1 hour under stirring at about 5° C. the white crystal is separated by filtration. The crystal is washed on the filter with 0.1 N hydrochloric acid and then with acetone, then, after purifying it by silica gel chromatography and drying it under vacuum, 190 mg of the product are obtained.

$^{195}$Pt-NMR in HCl 0.1 N/urea 0.5g/ml: -2417 ppm; -2668 ppm.

EXAMPLE 8

Synthesis of t,t,t-[BOCNH—(CH$_2$)$_6$—NH$_2$Pt(NH$_3$)$_2$H$_2$N—(CH$_2$)$_6$— NH$_2$Pt(NH$_3$)$_2$H$_2$N—(CH$_2$)$_6$—NH$_2$Pt(NH$_3$)$_2$H$_2$N—(CH2)$_6$—NHBOC]$^{+6}$.6NO$_3^-$ To a solution of 500 mg of t-[PtCl(NH$_3$)$_2$H$_2$N—(CH$_2$)$_6$—NHBOC]$^+$.NO$_3^-$ (intermediate (VI)—preparation 2) in 15 ml of dimethylformamide 156.4 mg of silver nitrate are added and the reaction mixture is kept in the darkness and at room temperature for 24 hours, then the mixture is filtered to eliminate the precipitated silver chloride.

The resulting solution is added to a solution of the intermediate of preparation 10 (310 mg) in 17 ml of anhydrous dimethylformamide and 0.872 ml of 1 N sodium hydroxide solution in methanol. After 36 hours the precipitated product is filtered and washed on the filter with dimethylformamide and then with tert-butyl methyl ether. The mother liquors are diluted with 200 ml of ethyl ether and kept 2 hours under stirring, then the solid is separated, obtaining 460 mg of the product.

EXAMPLE 9

Synthesis of t,t,t-[H$_3$N—(CH$_2$)$_6$—NH$_2$Pt(NH$_3$)$_2$H$_2$N—(CH$_2$)$_6$—NH$_2$Pt(NH$_3$)$_2$H$_2$N—(CH$_2$)$_6$—NH$_2$Pt(NH$_3$)$_2$ $_2$N—(CH$_2$)$_6$—NH$_3$]$^{+8}$.8NO$_3^-$—intermediate (X)

400 mg of the product of example 8 are dissolved in 36 ml of methanol and treated with 2.8 ml of 8 N hydrogen chloride solution in ethanol. After 2 days under stirring 320 mg of the product as hydrochloride salt are separated by filtration.

300 mg of the compound so obtained are dissolved in 10 ml of distilled water and treated with 284 mg of silver nitrate and the reaction mixture is kept in the darkness for 1 hour under stirring. After such a time, the mixture is filtered and the filtrate is added with 250 ml of acetone. After 2 hours under stirring 290 mg of the product are recovered by filtration.

EXAMPLE 10

Synthesis of t,t,t,t,t-[PtCl(NH$_3$)$_2$H$_2$N—(CH$_2$)$_6$—NH$_2$Pt—(NH$_3$)$_2$H$_2$N—(CH$_2$)$_6$—NH$_2$Pt(NH$_3$)$_2$H—$_2$N—(CH$_2$)$_6$—NH$_2$Pt(NH$_3$)$_2$H$_2$N—(CH$_2$)$_6$—NH$_2$PtCl(NH$_3$)$_2$]$^+$$_8$.8NO$_3^-$—compound (Ib)

To a solution of 250 mg of intermediate (X) (example 9) in 15 ml of dimethylformaide and 0.29 ml of 1 N sodium hydroxide solution in methanol, are added 10.92 ml of solution of t-[PtCl(NH$_3$)$_2$DMF]$^+$.NO$_3^-$ (intermediate (Va)) obtained according to preparation 8.

After 5 days under stirring the formed solid is filtered and it is washed on the filter with dimethylformamide and then with methanol. 203 mg of the product are obtained.

Such a compound may then be transformed into the corresponding hydrochloride salt as described in example 7.

EXAMPLE 11

According to the procedures described in the examples 5–7 or alternatively in the examples 8–10, the following penta-platinum complexes are obtained:

[Pt(MeCOO)(NH$_3$)$_2$H$_2$N—(CH$_2$)$_6$—NH$_2$Pt(NH$_3$)$_2$H$_2$N—(CH$_2$)$_6$—NH$_2$Pt—(NH$_3$)$_2$H$_2$N—(CH$_2$)$_6$—NH$_2$Pt(NH$_3$)$_2$H$_2$N—(CH$_2$)$_6$—NH$_2$Pt (MeCOO)—(NH$_3$)$_2$]$^{+6}$.6Cl$^-$;

[PtCl(MeNH$_2$)$_2$H$_2$N—(CH$_2$)$_6$—NH$_2$Pt(MeNH$_2$)$_2$H$_2$N—(CH$_2$)$_6$—NH$_2$Pt—(MeNH$_2$)$_2$H$_2$N—(CH$_2$)$_6$—NH$_2$Pt (MeNH$_2$)$_2$H$_2$N—(CH$_2$)$_6$—NH$_2$PtCl—(MeNH$_2$)$_2$]$^{+6}$.6Cl$^-$;

[Pt(Me$_2$SO)(NH$_3$)$_2$H$_2$N—(CH$_2$)$_6$—NH$_2$Pt(NH$_3$)$_2$H$_2$N—(CH$_2$)$_6$—NH$_2$(NH$_3$) $_2$H $_2$N—(CH$_2$)$_6$—NH$_2$Pt(NH$_3$) $_2$H$_2$N—(CH$_2$)$_6$—NH$_2$Pt(Me$_2$SO)— (NH$_3$)$_2$]$^{+8}$.8Cl$^-$;

[PtCl(Et$_2$NH)$_2$H$_2$N—(CH$_2$)$_6$—NH$_2$Pt(Et$_2$NH)$_2$H$_2$N—(CH$_2$)$_6$—NH$_2$Pt—(Et$_2$NH )$_2$H$_2$N—(CH$_2$)$_6$—NH$_2$Pt (Et$_2$NH)$_2$H$_2$N—(CH$_2$)$_6$—NH$_2$PtCl—(Et$_2$NH)$_2$]$^{+6}$.6NO$_3^-$;

[PtCl(NH$_3$)$_2$H$_2$N—(CH$_2$)$_2$—NH$_2$Pt(NH$_3$)$_2$H$_2$N—(CH$_2$)$_2$—NH$_2$Pt—NH$_3$)$_2$H$_2$N—(CH$_2$)$_2$—NH$_2$Pt(NH$_3$)$_2$H$_2$N—(CH$_2$)$_2$—NH$_2$PtCl—(NH$_3$)$_2$]$^{+6}$.6Cl$^-$;

[PtBr(NH$_3$)$_2$H$_2$N—(CH$_2$)$_7$—NH$_2$Pt(NH$_3$)$_2$H$_2$N—(CH$_2$)$_7$—NH$_2$Pt—(NH$_3$)$_2$H$_2$N—(CH$_2$)$_7$—NH$_2$Pt(NH$_3$)$_2$H$_2$N—(CH$_2$)$_7$—NH2PtBr—(NH$_3$)$_2$]$^+$6.6NO$_3^-$;

[PtCl(MeNH$_2$)$_2$H$_2$N—(CH$_2$)$_4$—NH$_2$Pt(MeNH$_2$)$_2$H$_2$N—(CH$_2$)$_4$—NH$_2$Pt—(MeNH$_2$)$_2$H$_2$N—(CH$_2$)$_4$—NH$_2$Pt (MeNH$_2$)$_2$H$_2$N—(CH$_2$)$_4$—NH$_2$PtCl—(MeNH$_2$)$_2$]$^{+6}$.6HSO$_4^-$;

[Pt(PrCOO)(NH$_3$)$_2$H$_2$N—(CH$_2$)$_3$—NH$_2$Pt(NH$_3$)$_2$H$_2$N—(CH$_2$)$_3$—NH$_2$Pt—(NH$_3$)$_2$H$_2$N—(CH$_2$)$_3$—NH$_2$Pt (NH$_3$)$_2$H$_2$N—(CH$_2$)$_3$—NH$_2$Pt(PrCOO)—(NH$_3$)$_2$]$^{+6}$.6Cl$^-$;

[PtCl(thiazole)$_2$H$_2$N—(CH$_2$)$_4$—NH$_2$Pt(NH$_3$)$_2$H$_2$N—(CH$_2$)$_4$—NH$_2$Pt—(NH$_3$)$_2$H$_2$N—(CH$_2$)$_4$—NH$_2$Pt (NH$_3$)$_2$H$_2$N—(CH$_2$)$_4$—NH$_2$PtCl(thiazole)$_2$]$^{+6}$.6HSO$_4^-$;

[PtCl(quinoline)$_2$H$_2$N—(CH$_2$)$_6$—NH$_2$Pt(NH$_3$)$_2$H$_2$N—(CH$_2$)$_6$NH$_2$Pt—(NH$_3$)$_2$H$_2$N—(CH$_2$)$_6$—NH$_2$Pt(NH$_3$)$_2$H$_2$N—(CH$_2$)$_6$—NH$_2$PtCl(quinoline)$_2$]$^{+8}$.8NO$_3^-$;

[PtCl(pyridine)$_2$H$_2$N—(CH$_2$)$_6$—NH$_2$Pt(NH$_3$)$_2$H$_2$N—(CH$_2$)$_6$—NH$_2$Pt—(pyridine)$_2$H$_2$N—(CH$_2$)$_6$—NH$_2$Pt (NH$_3$)$_2$H$_2$N—(CH$_2$)$_6$—NH$_2$PtCl(pyridine)$_2$]$^+$8.8Cl$^-$;

[PtCl(benzimidazole)$_2$H$_2$N—(CH$_2$)$_6$—NH$_2$Pt(NH$_3$)$_2$H$_2$N—(CH$_2$)$_6$—NH$_2$Pt(NH$_3$)$_2$H$_2$N—(CH$_2$)$_6$—NH$_2$Pt (NH$_3$)$_2$H$_2$N—(CH$_2$)$_6$—NH$_2$PtCl(bezimidazole )$_2$]$^+$ 8.8NO3$^-$.

What is claimed is:

1. A Compound of formula (I):

$$[PtXL_2NH_2-(CH_2)_n-NH_2-(PtL_2NH_2-(CH_2)_n-NH_2)_mPtXL_2]^+_{q}.q/zA^{-z} \quad (I)$$

wherein n is an integer from 2 to 7;

m is the integer 2 or 3;

X is selected in the group consisting of chlorine, bromine, iodine, ($C_1$–$C_4$) alkyl-carboxylate, di—($C_1$–$C_4$)-alkylsulfoxide;

L is independently selected in the group consisting of ammonia, ($C_1$–$C_8$)alkyl-amine, di ($C_1$–$C_8$) alkyl-amine or is an heterocycle selected in the group consisting in pyridine, quinoline, isoquinolines, imidazole, thiazole, pyrimidine, purine, acridine, pyrazole, benzimidazole, benzothiazole;

$A^{-z}$ is a pharmaceutically accetable anion, racemic mixtures, enantiometrs and diasteroisomers thereof.

2. A compound according to claim 1, in which m is the integer 2.

3. A compound according to claim 1, in which m is the integer 3.

4. A compound according to claim 1, in which X is selected in the group consisting of chlorine, bromine and iodine.

5. A compound according to claim 1, in which L is ammonia.

6. A compound according to claim 1, in which $A^{-z}$ is selected in the group consisting of chlorine, bromine, iodide, nitrate, sulfate, hydrogensulfate, perchlorate.

7. A compound according to claim 1, in which the various platinum cores of the same molecule are linked by the same α,ω-alkanediamine.

8. A compound according to claim 7, in which n is the integer 6.

9. A compound according to claim 1, in which the stereochemistry of the platinum atoms is trans.

10. A Compound according to claim 1, in which:

X is selected in the group consisting of chlorine, bromine and iodine;

L is ammonia;

$A^{-z}$ is selected in the group consisting o chloride, bromide, iodide, nitrate, sulfate, hydrogensulfate, perchlorate, and in which the stereochemistry of the ligands of the platinum atoms in trans.

11. A compound according to claim 1, of formula t,t,t,t-[PtCl(NH$_3$)$_2$H$_2$N-(CH$_2$)$_6$-NH$_2$Pt(NH$_3$)$_2$H$_2$N-(CH$_2$)$_6$- NH$_2$Pt(NH$_3$)$_2$H$_2$N-(CH$_2$)$_6$-NH$_2$PtCl(NH$_2$PtClCNH$_3$)$_2$ ]$^{+6}$.6Cl$^-$.3H$_2$O;

t,t,t,t t-[PtCl(NH$_3$)$_2$H$_2$N-(CH$_2$)$_6$-NH$_2$-Pt(NH$_3$)$_2$H$_2$N-(CH$_2$)$_6$-NH$_2$Pt(NH$_3$)$_2$H$_2$N-(CH$_2$)$_6$-NH$_2$Pt(NH$_3$)$_2$H$_2$N-(CH$_2$)$_6$-NH$_2$PtCl(NH$_3$)]$^+$8.8Cl$^-$;

t,t,t,t-[PtCl(NH$_3$)$_2$H$_2$N-(CH$_2$)$_6$-NH$_2$Pt(NH$_3$)$_2$H$_2$N-(CH$_2$)$_6$ -NH$_2$Pt(NH$_3$)$_2$H$_2$N-(CH$_2$)$_6$-NH$_2$Pt(NH$_3$)$_2$N-(CH$_2$)$_6$-NH$_2$PtCl(NH$_3$)$_2$]$^{+6}$.8.8NO3$^-$.

12. Process for the preparation of compounds of formula (Ia):

$$\left[ X-Pt(L)(L)-NH_2-Pt(H_2N)(L)(NH_2)-()_n-Pt(L)(NH_2)(H_2N)-NH_2-Pt(L)(L)-X \right]^{+(6+q')} \quad (Ia)$$

$$(6 + q') NO_3^-$$

wherein n is an integer from 2 to 7;

m is the integer 2 or 3;

X is selected in the group consisting of chlorine, bromine, iodine, ($C_1$–$C_4$)alkyl-carboxylate, di-($C_1$–$C_4$) alkylsulfoxide;

L is independently selected in the group consisting of ammonia, ($C_1$–$C_8$)alkyl-amine, di($C_1$–$C_8$)alkyl-amine or is an heterocylcle selected in the group consisting in pyridine, quinoline, isoquinoline, imidazole, thiazole, pyrimidine, purine, acridine, pyrazole, benzimidazole, benzothiazole;

$A^{-z}$ is a pharmaceutically accetable anion, racemic mixtures, enantiomers and diasteroisomers thereof, which comprises the following steps:

(a) activation of the bis-platinum complex of formula (II) through substitution of the two chlorine atoms with two molecules of dimethylformamide and subsequent reaction of the so obtained intermediate with two equivalents of mono-protected diamine of formula (III), to give the intermediate of formula (IV);

(b) removal of the two protecting groups of the amines from intermediate of formula (IV) and subsequent optional exchange of the counterion so obtained with nitrate ion to give the intermediate of formula (V);

(c) reaction of the intermediate of formula (V) with two equivalents of platinum complex of formula (Va) to give compounds of formula (Ia);

(d) optional transformation of one compound of formula (Ia) into another compound of formula (Ia) having a different counterion, by means of exchange reaction of said counterion with the wanted anion.

13. Process for the preparation of compounds of formula (Ib):

$$\left[ L-Pt(L)(L)-NH_2-(CH_2)-NH_2-Pt(L)(L)-NH_2-(CH_2)-NH_2-Pt(L)(L)-NH_2-(CH_2)-NH_2-Pt(L)(L)-NH_2-(CH_2)-NH_2-Pt(L)(L)-X \right]^{+(8+q')} \cdot 8 + q'/zA^{-z} \quad (Ib)$$

wherein n is an integer from 2 to 7;

m is the integer 2 or 3;

X is selected in the group consisting of chlorine, bromine, iodine, ($C_1$–$C_4$)alkyl-carboxylate, di-($C_1$–$C_4$) alkylsulfoxide; L is independently selected in the group consisting of ammonia, ($C_1$–$C_8$)alkyl-amine, di($C_1$–$C_8$)-alkyl-amine or is an heterocylcle selected in the group consisting in pyridine, quinoline, isoquinoline, imidazole, thiazole, pyrimidine, purine, acridine, pyrazole, benzimidazole, benzothiazole.

$A^{-z}$ is a pharmaceutically accetable anion, racemic mixtures, enantiomers and diasteroisomers thereof, which comprises the following steps:

(a) activation of the intermediate of formula (VI) through exchange of one chlorine atom with a molecule of dimethylformamide and subsequent reaction of the intermediate so obtained with one equivalent of intermediate of formula (VIa), to give the complex of formula (VII);

(b) removal of the aminic protecting group from the complex of formula (VII) and subsequent exchange reaction of the counterion so obtained with nitrate ion, obtaining the intermediate of formula (VIII);

(c) reaction of two equivalents of intermediate (VIII) with one equivalent of platinum complex of formula (VIIIa) to give a compound of formula (Ib);

(d) optional transformation of one compound of formula (Ib) into another compound of formula (Ib) having a different counterion by means of exchange reaction of said counterion with the wanted anion.

14. Process for the preparation of compounds of formula (Ib):

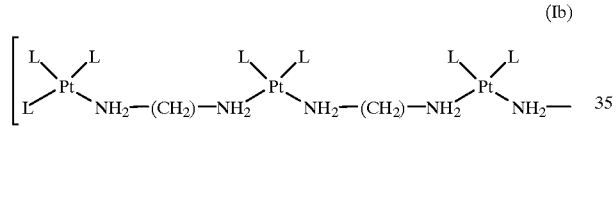

(Ib)

-continued

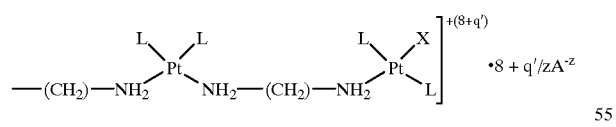

wherein n is an integer from 2 to 7;

m is the integer 2 or 3;

X is selected in the group consisting of chlorine, bromine, iodine, $(C_1-C_4)$alkyl-carboxylate, di-$(C_1-C_4)$alkylsulfoxide;

L is independently selected in the group consisting of ammonia, $(C_1-C_8)$alkyl-amine, di$(C_1-C_8)$alkyl-amine or is an heterocylcle selected in the group consisting in pyridine, quinoline, isoquinoline, imidazole, thiazole, pyrimidine, purine, acridine, pyrazole, benzimidazole, benzothiazole.

$A^{-z}$ is a pharmaceutically accetable anion, racemic mixtures, enantiomers and diasteroisomers thereof, which comprises the following steps:

a) reaction of the intermediate of formula (IX)

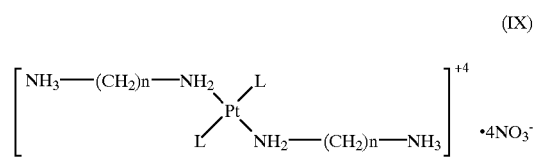

with two equivalents of intermediate of formula (VI)

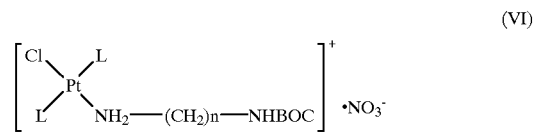

to give, after removal of the aminic protecting group present, the tri-platinum complex of formula (X)

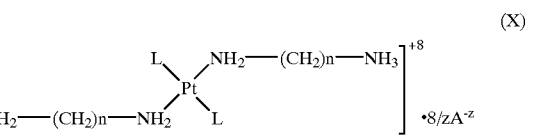

(b) optional exchange reaction of the anion $A^{-z}$ with nitrate anion;

(c) reaction of the tri-platinum complex obtained in step (b) with two equivalents of intermediate of formula (Va):

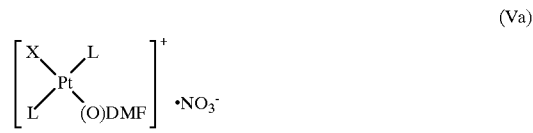

(d) optional transformation of one compound of formula (Ib) into another compound of formula (Ib) having a different counterion by means of the exchange reaction of said counterion with the wanted anion.

15. A pharmaceutical composition containing at least one compound according to claim 1 in admixture with pharmaceutically acceptable excipients.

16. of the compound according to claim 1, as an antitumor agent, the use comprises administering an effective amount of the compound within a predetermined proximity of a tumor cell.

17. Use according to claim 16, in which the tumors to be treated are tumors susceptible to the therapy with cis-platin.

18. Use according to claim to 16, in which the tumors to be treated are tumors that express resistance to cis-platin.

19. Use of the compound according to claim 1, in a method for treating parasytic diseases, the method comprises administering an effective amount of the compound to a patient suffering from a parasytic disease.

20. Use of the compound according to claim 1, in a method for the sensitization and enhancement of the radiations in radio-therapy, the method comprises administering an effective amount of the compound to a patient undergoing radio-therapy.

* * * * *